United States Patent

Fachinetti et al.

[11] 4,000,172
[45] Dec. 28, 1976

[54] THIO-DERIVATIVES OF VANADIUM AND PROCESSES FOR THEIR PREPARATION

[75] Inventors: Giuseppe Fachinetti, Fauglia; Carlo Floriani, Pisa, both of Italy

[73] Assignee: Snam Progetti S.p.A., Milan, Italy

[22] Filed: Apr. 29, 1975

[21] Appl. No.: 572,650

[30] Foreign Application Priority Data

May 17, 1974 Italy .............................. 22867/74

[52] U.S. Cl. ........................................ 260/429 CY
[51] Int. Cl.$^2$ .................................... C07F 9/00
[58] Field of Search ................. 260/429 R, 429 CY

[56] References Cited

UNITED STATES PATENTS

| | | | |
|---|---|---|---|
| 3,030,395 | 4/1962 | Giddings | 260/429.5 |
| 3,361,777 | 1/1968 | King | 260/429 |
| 3,644,447 | 2/1972 | Joshi | 260/429 R |

OTHER PUBLICATIONS

Coutts et al., Aus. J. Chem. - V19, 1377(1966).
Advances In Organometallic Chemistry, V9, 175–176 (1970).

*Primary Examiner*—Helen M. S. Sneed
*Attorney, Agent, or Firm*—Ralph M. Watson

[57] ABSTRACT

A thio-derivative of vanadium having the formula: $Vcp_2(SR)_n$, wherein cp is cyclopentadienyl, R is an alkyl, aryl or cycloalkyl radical and n is 1 or 2, is prepared by reacting vanadium di-cyclopentadiene with a disulphide represented by the formula: $S_2R_2$, wherein R has the meaning given above, in the presence of an inert solvent and in the temperature range of from room temperature to the boiling point of the solvent.

5 Claims, No Drawings

THIO-DERIVATIVES OF VANADIUM AND PROCESSES FOR THEIR PREPARATION

The present invention relates to new vanadium thio-derivatives and to methods for their preparation. More specifically the subject of the present invention is a new class of vanadium compounds, usable as polymerization catalysts, corresponding to the general formula $$Vcp_2(SR)_n$$

where cp is cyclopentadienyl, R is an alkyl, aryl, cycloalkyl radical, and $n$ is either 1 or 2.

The vanadium thio-derivatives corresponding to the above formula are obtained from vanadium dicyclopentadienyl ($Vcp_2$), which is reacted with a disulphide of formula $S_2R_2$, where R has the above-mentioned meaning.

The reaction can be represented by the following scheme:

1) $Vcp_2 + \frac{1}{2} R_2S_2 \rightarrow Vcp_2 SR$ (a)

2) $Vcp_2 + R_2S_2 \rightarrow Vcp_2 (SR)_2$ (b)

Naturally the first reaction can be continued without isolating compound (a), by simply adding di-sulphide to the same reaction vessel. The reactions are carried out in the presence of inert solvents, generally chosen from the aromatic hydrocarbons, at temperatures varying from room temperature to the boiling point of the solvent, which is preferred in case of the formation of product (b).

The yield of final product may be increased by adding to the reaction solution an aliphatic hydrocarbon and by cooling afterwards.

An alternative way for the preparation of compound (b), which represents a third aspect of the present invention, is the reaction between a halogen derivative of vanadium dicyclopentadienyl and a compound of the type RSM where M indicates a metal preferably an alkali metal. The reaction takes place according to this pattern 3) $Vcp_2X_2 + 2RSM \rightarrow Vcp_2 (SR)_2 + 2MX$ where X is the halogenide ion, preferably chloride.

The reaction takes place in the heterogeneous phase, generally between a suspension of the vanadium compound and the derivative of the alkali metal.

All the operating conditions will become evident from an examination of the following examples: all the operations here reported were conducted in inert atmosphere and the solvents were purified with known methods.

EXAMPLE 1

A solution consisting of 0.83 g (4.59 mmoles) of $Vcp_2$ (I) in 50 cm³ of toluene was treated with pure $Ph_2S_2$ (1.1 g equal to 5.05 moles) at room temperature.

The reaction was instantaneous and shortly a dark green solid soon crystallized. The overlying solution was then concentrated at reduced pressure and heptane was added. The final yield in $Vcp_2$ (SPh) (IV) was 75.1 percent.

Similarly, there were prepared the vanadium derivatives with n=1 where R is Me(II), Et(III), $PhCH_2$ (V).

The analytical results and some properties of the products are reported in the table.

EXAMPLE 2

A. A suspension in 50 cc of tetrahydrofurane of 1.4 g (5.55 moles) of $Vcp_2 Cl_2$ was added to 1.6 g (12.12 mmoles) of PhSNa, a dark green solution was soon formed. The solution thus obtained was evaporated at reduced pressure until dry, the green residue was extracted with 100 cc of toluene at 50° C and the toluene solution was concentrated to 30 cc. By adding heptane, a dark green solid was crystallized (yield 67.7 percent), which analyzed for $Vcp_2 (SPh)_2$ (VI).

B. 1.4 g (6.42 mmoles) of $Ph_2S_2$ were added to a solution in 20 cc of toluene of 0.7 g (2.41 mmoles) of IV. The resulting solution was refluxed to boil for about 15 minutes, then cooled and the amount of dark green crystals was increased by addition of heptane.

The yield of the compound (VI) was 89.2 percent.

Similarly the compound (VII) i.e. $Vcp_2(SCH_2Ph)_2$.

The test results and some properties are reported in the table.

In the above examples the quantities of reagents in excess in respect of the stoichiometric ratios of the reaction, remain in the reaction medium.

TABLE

| Complex | Analytic and magnetic results for vanadium thio-derivatives | | | eff/Tk' | PM*a* |
|---|---|---|---|---|---|
| | Analytic data % found (% calc.) | | | B.M.*b* | found (calc.) |
| | C | H | S | | |
| (II) Vcp₂(SMe) | 58.3 (57.9) | 6.2 (5.7) | 13.5 (14.0) | 2.71/292 | 255 (228) |
| (III) Vcp₂(SEt) | 59.5 (59.5) | 6.5 (6.2) | 12.6 (13.2) | | |
| (IV) Vcp₂(SPh) | 65.7 (66.2) | 5.5 (5.2) | 11.2 (11.0) | 2.75/293 | 290 (290) |
| (V) Vcp₂(SCH₂Ph) | 67.0 (67.1) | 5.5 (5.6) | 10.4 (10.5) | 2.76/293 | 318 (304) |
| (VI) Vcp₂(SPh)₂ | 66.0 (66.2) | 4.6 (5.0) | 16.5 (16.0) | 1.84/296 | |

*a*determined with crioscopic measurements in benzene
*b*results expressed for metal atom
The magnetic measurements were made with the Gouy balance

What we claim is:

1. A thio-derivative of vanadium represented by the formula $Vcp_2 (SR)_n$, wherein cp is cyclopentadienyl, R is a member of the group consisting of alkyl, aryl and cycloalkyl radicals and $n$ is 1 or 2.

2. The process of preparing a thio-derivative of vanadium claimed in claim 1, consisting of reacting vanadium-dicyclopentadienyl with a disulphide represented by the formula $S_2R_2$, wherein R is a member of the group consisting of alkyl, aryl and cycloalkyl radicals, in the presence of an aromatic hydrocarbon in the temperature range of from room temperature to the boiling temperature of said aromatic hydrocarbon.

3. The process of preparing a thio-derivative of vanadium represented by the formula $Vcp_2SR$, wherein cp is cyclopentadienyl and R is a member of the group consisting of alkyl, aryl and cycloalkyl radicals, consisting of reacting vanadium-dicyclopentadienyl with a disulphide as claimed in claim 9, wherein the reaction is carried out between vanadium-dicyclopentadienyl and said disulphide in the ratio 2:1.

4. The process of preparing a thio-derivative of vanadium represented by the formula $Vcp_2(SR)_2$, wherein cp is cyclopentadienyl and R is a member of the group consisting of alkyl, aryl and cycloalkyl radicals, consisting of reacting vanadium-dicyclopentadienyl with a disulphide as claimed in claim 9, wherein the reaction is carried out between vanadium-dicyclopentadienyl and said disulphide in the ratio 1:1.

5. The method of preparing a thio-derivative of vanadium claimed in claim 8 which is represented by the formula $Vcp_{2(SR)2}$, wherein cp is cyclopentadienyl and R is a member of the group consisting of alkyl, aryl and cycloalkyl, consisting of reacting a halogen of vanadium-dicyclopentadienyl with a compound represented by the formula RSM, wherein R has the meaning given above and M is an alkali metal, in the presence of an aromatic hydrocarbon in the temperature range of from room temperature to the boiling temperature of said aromatic hydrocarbon.

* * * * *

UNITED STATES PATENT AND TRADEMARK OFFICE
CERTIFICATE OF CORRECTION

PATENT NO. : 4,000,172
DATED : December 28, 1976
INVENTOR(S) : Giuseppe Fachinetti and Carlo Floriani It is certified that error appears in the above-identified patent and that said Letters Patent are hereby corrected as shown below:

Column 3, line 1, Correct "claim 9" to read --claim 2--.

line 9, Correct "claim 9" to read --claim 2--.

Column 4, line 2, Correct "claim 8" to read --claim 1--.

line 3, Correct "$Vcp_{2(SR)}2$" to read --$Vcp_2(SR)_2$--.

Signed and Sealed this ninth Day of August 1977

[SEAL]

Attest:

RUTH C. MASON
*Attesting Officer*

C. MARSHALL DANN
*Commissioner of Patents and Trademarks*